United States Patent [19]

Ravaska

[11] Patent Number: 5,034,509
[45] Date of Patent: Jul. 23, 1991

[54] METHOD FOR IMPROVING THE COLOR AND THE STABILITY OF THE COLOR OF CARBOXYLIC ACID OR A MIXTURE OF THE SAME

[76] Inventor: Matti E. Ravaska, Sepänkatu 9 B 10, SF-90100 Oulu 10, Finland

[21] Appl. No.: 430,957

[22] Filed: Nov. 1, 1989

Related U.S. Application Data

[63] Continuation of Ser. No. 99,705, Sep. 21, 1987, abandoned, which is a continuation of Ser. No. 610,192, May 16, 1984, abandoned, which is a continuation-in-part of Ser. No. 519,629, Aug. 2, 1983, abandoned.

[30] Foreign Application Priority Data

Aug. 17, 1982 [FI] Finland ................................. 822853

[51] Int. Cl.$^5$ ........................... C09F 1/02; C11B 5/00; C07C 63/06; C07C 55/14
[52] U.S. Cl. .................................. 530/208; 260/419; 260/420; 562/494; 562/593
[58] Field of Search .................. 260/419, 420; 530/208

[56] References Cited

U.S. PATENT DOCUMENTS

| | | | |
|---|---|---|---|
| 2,374,975 | 5/1945 | Borglin | 530/208 |
| 3,168,569 | 2/1965 | Matell | 530/208 X |
| 3,377,333 | 4/1968 | Ciesielski et al. | 530/206 |
| 3,551,404 | 12/1970 | Watkins | 530/205 |
| 3,804,819 | 4/1974 | Wengrow et al. | 530/208 |
| 4,126,604 | 11/1978 | Alford et al. | 530/209 |
| 4,222,933 | 9/1980 | Alford | 530/213 |

FOREIGN PATENT DOCUMENTS 2072656 10/1981 United Kingdom ................ 260/420

*Primary Examiner*—Carolyn S. Elmore

[57] ABSTRACT

The invention relates to a method for improving the color and the stability of the color of carboxylic acid or a mixture of the same by treating the carboxylic acid or its mixture with a hydride-yielding substance at an elevated temperature and by distilling the mixture thus obtained. The color and the stability of the color of the distillate thus obtained are better than the corresponding quantities of a distillate of untreated carboxylic acid or an untreated mixture of the same. Sodium borohydride and lithium aluminum hydride are preferred hydride-yielding substances. The method according to the invention can be applied to all carboxylic acids, advantageously to fatty acids and resin acids.

3 Claims, No Drawings

METHOD FOR IMPROVING THE COLOR AND THE STABILITY OF THE COLOR OF CARBOXYLIC ACID OR A MIXTURE OF THE SAME

This is a continuation of co-pending application Ser. No. 099,705, filed Sept. 21, 1987, abandoned, which in turn was a continuation of U.S. application Ser. No. 610,192, filed May 16, 1984, now abandoned, which, in turn, was a continuation-in-part of U.S. application Ser. No. 519,629, filed Aug. 2, 1983, abandoned.

BACKGROUND OF THE INVENTION

The present invention relates to a method for improving the color and the stability of the color of carboxylic acid or a mixture of the same.

The color and the stability of the color of carboxylic acids, mainly fatty acids, have commonly been improved by using a bleaching-earth treatment, in which bleaching earth is added at 1–20 % to fatty acid and filtered off after mixing. Such a treatment is difficult on an industrial scale, since it requires a mixing tank and a filter. Furthermore, the material being treated must be fluid at relatively low temperatures, i.e. at below 100° C., in order that the treatment should not decompose the carboxylic acids. In addition, some of the product remains in the bleaching earth after the filtration, which means losses of material.

Because of the drawbacks of the above-mentioned method, endeavors have been made to find other methods. U.S. Pat. No. 3,551,404 describes a method in which pine resin is heated at 200–300° C. for 1–20 hours and is thereafter distilled. The color and the odor are thereby improved.

U.S. Pat. No. 3,377,333 describes a method in which phenol sulfides are added to crude tall oil in connection with vacuum distillation. However, sulfur compounds have a disproportioning effect on resin acids and an isomerizing effect on fatty acids, a fact which may be disadvantageous in distillation and in the intended use of the final products.

U.S. Pat. Nos. 4,126,604 and 4,222,933 describe methods in which zinc and iodine, and respectively zinc and boric acid, are added to fatty acids and to resin acids. They have a disadvantage in that it is necessary to add two different substances to the process and that iodine and acids in general have a decarboxylating effect on resin acids and fatty acids.

SUMMARY OF THE INVENTION

The object of the present invention is to provide a method by which these difficulties can be overcome, and this is accomplished according to the invention by treating the carboxylic acid or the mixture of the same with a hydride-yielding substance, and distilling the mixture thus obtained in order to obtain a carboxylic acid or its mixture, with improved color or an improved stability of color.

The present invention is particularly advantageous for improving the color of higher boiling carboxylic acids, e.g., acids or mixtures of acids which are solid at temperatures below 100° C. It is these acids which are most colored and consequently most in need of color improvement. Methods carried out at lower temperatures (e.g., 80° C. or less) are only effective for carboxylic acids which are liquid at those temperatures. The lower boiling acids are generally transparent and therefore less in need of color improvement. At reaction temperatures in excess of 100° C., the hydride reaction is more effective and can be accompanied by a vigorous evaluation of hydrogen. By conducting the method of the present invention under a vacuum (e.g., at pressures less than 1 atm.), the hydrogen which is produced as a byproduct of the hydride reaction is easily removed without the danger of explosion.

DESCRIPTION OF THE PREFERRED EMBODIMENTS

According to one preferred embodiment, the hydride-yielding substance is fed into the distillation process, for example the tall oil distillation process, at a point prior to the distillation column from which the product is withdrawn, i.e. into the pipe system, a tank, the product column, or circulation through its trays. Thereby the color and the stability of the color of the product, an organic acid, are improved.

Alkali borohydrides and alkali aluminum hydrides are commonly used for reducing peroxides, aldehydes and ketones to alcohols, and they can be assumed also to constitute color-producing groups in various carboxylic acids. It is assumed that compounds containing these groups are present in very small quantities in the product, but nevertheless they are believed to cause distinct darkening of the product.

When hydrides are used with carboxylic acids, an expert would, however, expect that borohydrides or aluminum hydrides would first react with the hydrogen of the carboxyl group, thereby forming gaseous hydrogen, and thus would be incapable of or insufficient for reducing the color-producing groups.

It has, however, now been surprisingly observed that, when carboxylic acid is mixed at a high temperature with a hydride-yielding substance and distilled, the color and the stability of the color of the distillate of the thus treated carboxylic acid are better than the respective quantities of the distillate of an untreated carboxylic acid.

The improving effect of the hydride on the color and the stability of color can be considered to extend to carboxylic acids in general. It is possible to use aliphatic, alicyclic and aromatic carboxylic acids. The acids can be saturated or unsaturated, or they can be mono-, di- or polycarboxylic acids. The method according to the invention is also suitable for improving the color and the stability of the color of mixtures of carboxylic acids and mixtures principally containing carboxylic acids. Advantageous carboxylic acids and mixtures of carboxylic acids include fatty acids such as tallow fatty acid and pine fatty acid, resin acids, benzoic acid, adipinic acid, tall oil, pine resin, and gum rosin.

It is possible to use borohydrides or aluminum hydrides as hydride-yielding substances. Sodium borohydride is more recommended, since it is less expensive than, for example, lithium aluminum hydride and since it is a chemically more stable compound. It does not decompose until above 400° C. and does not ignite even at 300° C. on a hot plate. The amount to be used for improving the color and the stability of the color of carboxylic acids depends on the particular carboxylic acid or mixture to be treated. The most suitable amount is within the range 1–10000 ppm. The amount most suitable in the distillation of tall oil is 200–500 ppm, depending on the feeding point and the quality of the raw material.

A borohydride treatment can be carried out by adding the borohydride to the carboxylic acid at a temperature in excess of 100° C., preferably in excess of 150° C., and most preferably in the range of about 200° to 250° C. In many cases it is desirable to conduct the borohydride treatment at the temperature at which the distillation is also carried out. It is advantageous to allow a sufficient reaction time for the borohydride. A reaction time of up to 2 hours has in general been used in laboratory experiments, but this so-called preliminary reaction is not necessary. When borohydride is fed into a distillation column system, it is advantageous to select a feeding point which allows a sufficiently long retention time prior to distillation. On the other hand, the use of lithium aluminum hydride is limited by the fact that it decomposes at 125° C., and so it is perhaps advisable to add it to the carboxylic acid at a temperature below this value.

The distillation can be carried out at either a lowered or normal pressure, depending on the acid used. When hydrides react with carboxylic acids, a dark color is produced. These compounds which produce a dark color are left in the distillation residue, and the color and the stability of the color of the distillate are improved.

The color can be defined in several different ways. In the present invention the so-called Gardner color scale is used, in which the intensity of the color is divided into 18 units, color 1 being the whitest and color 18 being the darkest. This scale is used commonly for fatty acids, since they are in general substances fluid at room temperature. The U.S. Rosin Standard method, in which the color scale is X, WW, WG, N, M, K, I, H, G, F, E, D, is used for the definition of the color of solid, non-transparent substances such as resin acids. In this scale, X is the whitest and D the darkest color.

There is no standard method for the determination of the stability of color. In the present invention the stability of the color of fatty acids is determined by keeping carboxylic acid in an open test tube in an air space in a heat cupboard at 200° C. for 1 hour, and by determining the color thereafter. The stability of the color of resin acid or a solid carboxylic acid, on the other hand, is determined either by keeping the sample in an open test tube at 180° C. for 16 hours or at 200° C. for 6½ hours and by determining the color thereafter.

The method according to the invention is described in greater detail with the aid of examples.

EXAMPLE 1

The carboxylic acid used was tallow fatty acid, which contains the following types of fatty acids.

| C14:0 myristic acid | 3% saturated fatty acid |
|---|---|
| C16:0 palmitic acid | 29% saturated fatty acid |
| C18:0 stearic acid | 18.5% saturated fatty acid |
| C18:1 oleic acid | 46.5% unsaturated fatty acid |
| C18:2 linolic acid | 3% unsaturated fatty acid |

100 g tallow fatty acid was heated to 250° C., whereafter 0.05 g sodium borohydride was added cautiously in small batches while stirring.

The addition borohydride causes foaming. The mixture was stirred for 2 hours at 250° C. Thereafter the mixture was distilled under a vacuum.

The color and the stability of the color of the distillate were determined. In addition, a reference experiment was carried out in which tallow fatty acid was distilled over in a vacuum. The results were as follows:

|  | Color | Stability of color 1 hr. at 200° C. |
|---|---|---|
| Only distillation over | 1+ | 6− |
| NaBH₄-treated distilled product | 2− | 4− |

EXAMPLE 2

The carboxylic acid used was pine fatty acid, which contains principally unsaturated fatty acids. Its analysis is as follows:

| C16:0 palmitic acid | 0.5% saturated fatty acid |
|---|---|
| C18:0 stearic acid | 1.4% saturated fatty acid |
| C20:0 arachidic acid | 0.6% saturated fatty acid |
| C18:1 oleic acid | 27% unsaturated fatty acid |
| C18:2 linolic acid | 41% unsaturated fatty acid |
| C18:3 pinoleic acid | 10% unsaturated fatty acid |

In addition, pine fatty acid contains unknown unsaturated fatty acids.

This experiment was carried out in the same way as in Example 1. The results were as follows:

|  | Color | Stability of color 1 hr. at 200° C. |
|---|---|---|
| Only distillation over | 3½ | 6½ |
| NaBH₄-treated distilled product | 3− | 4− |

EXAMPLE 3

The feed into the fatty acid column in a tall oil distillation plant contains resin acids about 15%, neutral substance about 6%, and the remainder is fatty acids. Using this as the initial material, the experiment was carried out in the same manner as in Example 1. The results were as follows:

|  | Color | Stability of color 1 hr. at 200° C. |
|---|---|---|
| Only distillation over | 4½ | 6½ |
| NaBH₄-treated distilled product | 3½ | 4½ |

EXAMPLE 4

100 g crude tall oil was heated to 200° C., at which 0.05 g NaBH₄ was added, and the mixture was stirred for 2 hours at 200° C. Thereafter the mixture was distilled over in a vacuum, and the color and the stability of the color of the distillate were determined. In addition, a reference experiment was carried out, in which crude tall oil was distilled over in a vacuum, and the color and the stability of the color of the distillate were also determined. The results were as follows:

|  | Color | Stability of color 1 hr. at 200° C. |
|---|---|---|
| Only distillation over | 10− | 11− |
| NaBH₄-treated | 8+ | 9− |

|  | Color | Stability of color 1 hr. at 200° C. |
| --- | --- | --- |
| distilled product | | |

EXAMPLE 5

100 g pine resin, which is a mixture of cyclic, unsaturated carboxylic acids, was heated to 250° C., at which 0.05 g sodium borohydride was added, and the mixture was stirred at the said temperature for 2 hours. Thereafter the product was distilled over in a vacuum. The color and the stability of the color of the distillate were determined. For reference, pine resin was distilled over without treatment with chemicals, and the color and the stability of the color of this distillate were also determined.

The results were as follows:

|  | Color | Stability of color 16 hr. at 180° C. |
| --- | --- | --- |
| Ordinary distillation over | X-WW | I-H |
| NaBH$_4$-treated distilled product | whiter than X | M-K |

EXAMPLE 6

100 g gum rosin was heated to 250° C., at which 0.05 g sodium borohydride was added, and the mixture was stirred at 250° C. for 2 hours. Thereafter the product was distilled over in a vacuum, and the color and the stability of the color of the distillate were determined. Likewise, gum rosin, which had been used as the initial substance, was distilled over in a vacuum, and the color and the stability of the color of the distillate were determined.

|  | Color | Stability of color 16 hr. at 180° C. |
| --- | --- | --- |
| Distilled-over gum rosin | WG-N | G-F |
| NaBH$_4$-treated distilled product | X-WW | H-G |

EXAMPLE 7

The carboxylic acid used was benzoic acid. 100 g benzoic acid was heated to 230° C., whereafter 0.05 g sodium borohydride was added, and the mixture was stirred at 230° C. for 2 hours. Thereafter the product was distilled over in a vacuum. For reference, benzoic acid was distilled under the same conditions as the NaBH$_4$-treated product.

The results were as follows:

|  | Color | Stability of color 6¼ hr. at 200° C. |
| --- | --- | --- |
| Reference | 1½ | 3— |
| NaBH$_4$-treated, distilled-over benzoic acid | 1— | 2— |

EXAMPLE 8

The carboxylic acid used was adipinic acid, which is a saturated dicarboxylic acid. 0.01 g sodium borohydride was added to 100 g adipinic acid and the mixture was distilled at a temperature of 150–180° C. without any preliminary reactions. For reference, adipinic acid was distilled under the same conditions as above.

The results were as follows:

|  | Color | Stability of color 1 hr. at 200° C. |
| --- | --- | --- |
| Ordinary distillation over | 1¼ | 3+ |
| Product distilled with NaBH$_4$ | 1¼ | 3— |

EXAMPLE 9

100 g pine fatty acid and 0.05 g LiAlH$_4$ were mixed and the temperature was raised to 250° C., at which stirring was continued for 2 hours. Thereafter the product was distilled over in a vacuum. For reference, the same initial substance was distilled over in a vacuum.

The results were as follows:

|  | Color | Stability of color 1 hr. at 200° C. |
| --- | --- | --- |
| Ordinary distillation | 5— | 7¼ |
| LiAlH$_4$-treated and distilled-over product | 4— | 5— |

EXAMPLE 10

In the following experiment, the effect of the amounts of NaBH$_4$ on the color and the stability of the color of pine fatty acid was studied. The experiments were carried out as in Example 1.

The results are given in the table below.

| NaBH$_4$ amount used | Color | Stability of color |
| --- | --- | --- |
| 0 ppm | 5— | 7— |
| 1 ppm | 4— | 6— |
| x)3 ppm | 4+ | 6¼ |
| 5 ppm | 3+ | 5— |
| 50 ppm | 3— | 5¼ |
| 500 ppm | 3— | 4— |
| 5 000 ppm | 4+ | 7— |
| xx)10 000 ppm | 4¼ | 6¼ | x)LiAlH$_4$ was used instead of NaBH$_4$.
xx)In this experiment, no preliminary reaction was used, and the distillation was carried out immediately after the addition of NaBH$_4$.

What is claimed is:

1. A method for improving the color and stability of the color of an acid selected from the group consisting of pine resin and pine fatty acid comprising:
   the separate steps of
   treating said acid with a hydride-providing substance at a temperature of from about 200° to 250° C. for about 2 hours, and
   subsequently distilling the resultant mixture under a vacuum whereby a distillate having improved color and improved stability of color is obtained.

2. The method of claim 1, in which the hydride-providing substance is a borohydride or an aluminum hydride.

3. The method of claim 2, in which the hydride-providing substance is sodium borohydride or lithium aluminum hydride.

* * * * *

UNITED STATES PATENT AND TRADEMARK OFFICE
CERTIFICATE OF CORRECTION

PATENT NO. : 5,034,509

DATED : July 23, 1991

INVENTOR(S) : Matti E. Ravaska

It is certified that error appears in the above-identified patent and that said Letters Patent is hereby corrected as shown below:

ON THE TITLE PAGE:

Item "[76]" should be --[75]--.

The assignee's name is missing from the cover sheet and should be added --[73] Assignee: Veitsiluoto Oy, Finland.

Signed and Sealed this

Tenth Day of November, 1992

Attest:

DOUGLAS B. COMER

*Attesting Officer*   *Acting Commissioner of Patents and Trademarks*